(12) United States Patent  
Lukasik

(10) Patent No.: US 8,444,921 B2  
(45) Date of Patent: May 21, 2013

(54) MOLECULAR SEPARATORS, CONCENTRATORS, AND DETECTORS PREPARATORY TO SENSOR OPERATION, AND METHODS OF MINIMIZING FALSE POSITIVES IN SENSOR OPERATIONS

(75) Inventor: Stephen J. Lukasik, Falls Church, VA (US)

(73) Assignee: Advanced Concepts and Technologies International, L.L.C., Waco, TX (US)

( * ) Notice: Subject to any disclaimer, the term of this patent is extended or adjusted under 35 U.S.C. 154(b) by 13 days.

(21) Appl. No.: 13/441,301

(22) Filed: Apr. 6, 2012

(65) Prior Publication Data

US 2013/0024134 A1 Jan. 24, 2013

Related U.S. Application Data

(62) Division of application No. 12/403,989, filed on Mar. 13, 2009, now Pat. No. 8,192,685.

(60) Provisional application No. 61/111,048, filed on Nov. 4, 2008.

(51) Int. Cl.  
*G01N 33/00* (2006.01)  
*G06F 19/00* (2006.01)

(52) U.S. Cl.  
USPC ............... 422/67; 422/83; 340/500; 340/522; 702/188; 703/11; 703/12

(58) Field of Classification Search  
None  
See application file for complete search history.

(56) References Cited

U.S. PATENT DOCUMENTS

| | | | |
|---|---|---|---|
| 4,347,732 A | 9/1982 | Leary |
| 4,542,640 A | 9/1985 | Clifford |
| 5,626,650 A | 5/1997 | Rodriguez et al. |
| 6,511,527 B2 | 1/2003 | Yang et al. |
| 6,528,020 B1 | 3/2003 | Dai et al. |
| 6,905,655 B2 | 6/2005 | Gabriel et al. |
| 6,997,039 B2 | 2/2006 | Rao et al. |
| 7,013,708 B1 | 3/2006 | Cho et al. |
| 7,014,829 B2 | 3/2006 | Yanagisawa et al. |
| 7,034,677 B2 | 4/2006 | Steinthal et al. |
| 7,074,260 B2 | 7/2006 | Lee et al. |
| 7,097,694 B1 | 8/2006 | Jaroszcyk et al. |
| 7,112,816 B2 | 9/2006 | Schlaf et al. |
| 7,166,325 B2 | 1/2007 | Dai et al. |

(Continued)

FOREIGN PATENT DOCUMENTS

| FR | 2873111 | 1/2006 |
|---|---|---|
| WO | WO 03/008931 | 1/2003 |
| WO | WO/2008/133656 | 11/2008 |

OTHER PUBLICATIONS

Chopra, S., et al., "Selective gas detection using a carbon nanotube sensor", Applied Physics Letters, vol. 83, No. 11, (pp. 2280-2282) Sep. 15, 2003.

(Continued)

*Primary Examiner* — P. Kathryn Wright  
(74) *Attorney, Agent, or Firm* — Whitham Curtis Christofferson & Cook, PC

(57) ABSTRACT

As an elegant solution for minimizing false positives returned by a sensor tuned to an analyte molecule, filters constructed of carbon nanotubes are positioned relative to the sensor to limit the sensor to being exposed to molecules within a defined range of sizes, with too-big molecules being excluded from reaching the sensor by one filter, and too-small molecules being pumped out through another, finer filter before the sensor is operated.

7 Claims, 7 Drawing Sheets

U.S. PATENT DOCUMENTS

| | | |
|---|---|---|
| 7,171,312 B2 | 1/2007 | Steinthal et al. |
| 7,312,095 B1 | 12/2007 | Gabriel et al. |
| 7,318,908 B1 | 1/2008 | Dai |
| 7,342,479 B2 | 3/2008 | Glatkowski et al. |
| 7,344,691 B2 | 3/2008 | Chen et al. |
| 7,355,216 B2 | 4/2008 | Yang et al. |
| 7,374,900 B2 | 5/2008 | Soukharev et al. |
| 7,385,266 B2 | 6/2008 | Segal et al. |
| 7,416,699 B2 | 8/2008 | Dai et al. |
| 7,426,848 B1 | 9/2008 | Li et al. |
| 2003/0154865 A1 | 8/2003 | Zornes |
| 2004/0200734 A1 | 10/2004 | Co et al. |
| 2005/0040090 A1 | 2/2005 | Wang et al. |
| 2005/0142662 A1 | 6/2005 | Bonne |
| 2005/0169830 A1 | 8/2005 | Richard et al. |
| 2006/0085367 A1 | 4/2006 | Genovese |
| 2006/0088848 A1 | 4/2006 | Noca et al. |
| 2006/0169585 A1 | 8/2006 | Nagahara et al. |
| 2006/0188934 A1 | 8/2006 | Chang et al. |
| 2006/0263255 A1 | 11/2006 | Han et al. |
| 2006/0269927 A1 | 11/2006 | Lieber et al. |
| 2006/0275914 A1 | 12/2006 | Henley et al. |
| 2007/0009379 A1 | 1/2007 | Bau et al. |
| 2007/0051240 A1 | 3/2007 | Lin |
| 2007/0099311 A1 | 5/2007 | Zhou et al. |
| 2007/0229834 A1 | 10/2007 | Patel et al. |
| 2007/0292877 A1 | 12/2007 | Dimitrov |
| 2008/0017791 A1 | 1/2008 | Wilks et al. |
| 2008/0084561 A1 | 4/2008 | Patel et al. |
| 2008/0145616 A1 | 6/2008 | Gharib et al. |
| 2008/0169921 A1 | 7/2008 | Peeters |
| 2008/0223795 A1 | 9/2008 | Bakajin et al. |
| 2008/0286466 A1 | 11/2008 | Holmes et al. |

OTHER PUBLICATIONS

Holt, J.K., et al., "Fast Mass Transport Through Sub-2-Nanometer Carbon Nanotubes", Science, vol. 312 (pp. 1034-1037) May 19, 2006.

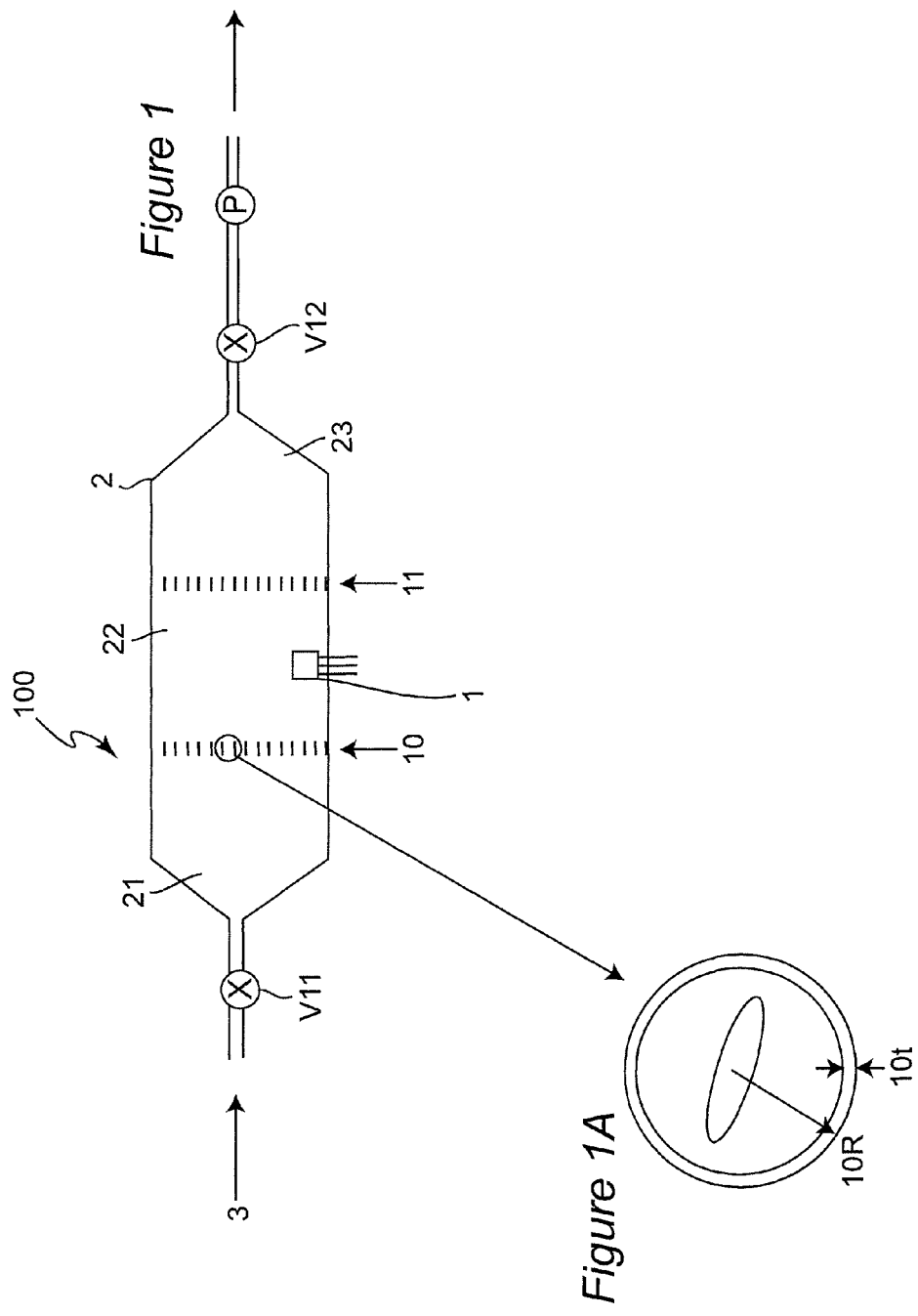

| | Name | CAS # | MW (g/mol) | MP (°C) | BP (°C) | VP in ATM | Formula | Max Diameter (Å) |
|---|---|---|---|---|---|---|---|---|
| Wood Smoke | styrene | 100-42-5 | 104.1491 | -31 | 145 | 8.42E-03 | C8H8 | 7.7728 |
| Explosion site | styrene | 100-42-5 | 104.1491 | -31 | 145 | 8.42E-03 | C8H8 | 7.7728 |
| Cigarette smoke | styrene | 100-42-5 | 104.1491 | -31 | 145 | 8.42E-03 | C8H8 | 7.7728 |
| Low risk TIC | isobutyl chloroformate | 543-27-1 | 136.58 | | 128.8 | 1.10E-02 | C5H9ClO2 | 7.7912 |
| Fresh cut grass | Terpinen-4-ol | 562-74-3 | 154.2493 | | 209 | 5.62E-05 | C10H18O | 7.812062 |
| Low risk TIC | hexachlorocyclopentadiene | 77-47-4 | 272.77 | -9 | 239 | 7.89E-05 | C5Cl6 | 7.82378 |
| Diesel Vapor | propyl benzene | 103-65-1 | 120.19 | -99.6 | 159.2 | 4.50E-03 | C9H12 | 7.86866 |
| Diesel Vapor | Ethyl Benzene | 100-41-4 | 106.167 | -95 | 136 | 1.26E-02 | C8H10 | 7.87071 |
| Wood Smoke | Ethyl Benzene | 100-41-4 | 106.165 | -94.9 | 136.1 | 1.26E-02 | C8H10 | 7.87071 |
| Paint | Ethyl Benzene | 100-41-4 | 106.165 | -94.9 | 136.1 | 1.26E-02 | C8H10 | 7.87071 |
| Explosion site | Ethyl Benzene | 100-41-4 | 106.165 | -94.9 | 136.1 | 1.26E-02 | C8H10 | 7.87071 |
| Fresh cut grass | Limonene | 5989-27-5 | 136.24 | -74.3 | 176 | 2.61E-03 | C10H16 | 7.94577 |
| Diesel Vapor | ethyl cyclohexane | 1678-91-7 | 112.22 | -111 | 132 | 1.68E-02 | C8H16 | 7.95452 |
| Low risk TIC | ethyl chlorothioformate | 2941-64-2 | 124.59 | | 136 | 5.33E-03 | C3H5ClOS | 8.02657 |
| Low risk TIC | tetraethyl lead | 78-00-2 | 323.44 | -136 | 202 | 3.42E-04 | C8H20Pb | 8.170964 |
| nerve agent | tabun | 77-81-6 | 162.13 | -50 | 248 | 9.21E-05 | C5H11N2O2P | 8.218646 |
| AFFF | Nonafluorobutanesulfonyl fluoride (example fluorochemical surfactant) | 375-72-4 | 302.09 | | 64 | 2.21E-01 | C4F10O2S | 8.2855 |
| High risk TIC | diethyl methylphosphonate | 683-08-9 | 152.1287 | | 194 | 1.75E-05 | C5H13O3P | 8.32921 |
| Ben Gay | Methyl Salicylate | 119-36-8 | 152.1473 | -8 | 222.9 | 4.51E-05 | C8H8O3 | 8.46591 |
| Cigarette smoke | nicotine | 54-11-5 | 162.2316 | -79 | 247 | 5.00E-05 | C10H14N2 | 8.50866 |
| Low risk TIC | allyl isothiocyanate | 57-06-7 | 99.16 | -80 | 152 | 4.87E-03 | C4HSNS | 8.52939 |
| AFFF | propylene glycol t-butyl ether | 57018-52-7 | 132.2 | -85 | 151 C | 6.32E-03 | C7H16O2 | 8.591522 |
| nerve agent | soman | 96-64-0 | 182.17 | -24 | 198 | 5.26E-04 | C7H16FO2P | 8.6444 |
| Glue/Adh | hexane | 110-54-3 | 86.1754 | -95.3 | 68.7 | 1.99E-01 | C6H14 | 8.70454 |
| nerve agent | cyclosarin | 329-99-7 | 180.2 | -30 | 239 | 5.79E-05 | | 8.752936 |
| Fresh cut grass | p-Cymene | 99-87-6 | 134.221 | -68 | 177.1 | 1.92E-03 | 0.8573 | 8.84658 |
| Fresh cut grass | α-Terpinene | 99-86-5 | 136.24 | <-25 | 175 | 2.18E-03 | C10H16 | 8.86118 |
| Low risk TIC | n-butyl chloroformate | 592-34-7 | 136.58 | <-70 | 142 | 8.61E-03 | C5H9ClO2 | 8.876392 |
| Low risk TIC | n-butyl isocyanate | 111-36-4 | 99.13 | <-70 | 115 | 2.32E-02 | C5H9NO | 8.95968 |
| Fresh cut grass | γ-Terpinene | 99-85-4 | 136.24 | -10 | 183 | 1.43E-03 | C10H16 | 8.99 |
| Mineral brake fluid | Diethylene glycol | 111-46-6 | 106.12 | -10.4 | 245.8 | 7.50E-06 | C4H10O3 | 9.04998 |
| Fresh cut grass | α-Cubebene | 17699-14-8 | 204.35 | | 245.5 | | C15H24 | 9.08694 |
| High risk TIC | thiodiglycol | 111-48-8 | 122.186 | -10.2 | 282 | 4.25E-06 | C4H10O2S | 9.11189 |
| Diesel Exhaust | anisaldehyde | 123-11-5 | 136.15 | 0 | 248 | 4.33E-05 | C8H8O2 | 9.13641 |
| Diesel Vapor | 3-methyl heptane | 589-81-1 | 114.23 | -121 | 119 | 2.58E-02 | C8H18 | 9.25804 |

*Figure 2*

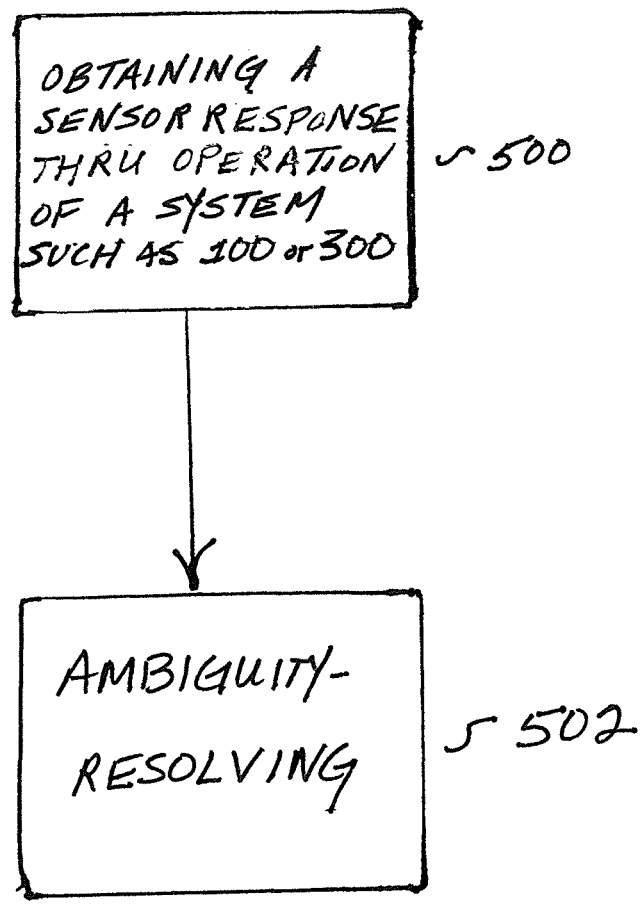

MOLECULAR SEPARATORS, CONCENTRATORS, AND DETECTORS PREPARATORY TO SENSOR OPERATION, AND METHODS OF MINIMIZING FALSE POSITIVES IN SENSOR OPERATIONS

RELATED APPLICATION

This application claims benefit of U.S. provisional application Ser. No. 61/111,048 filed Nov. 4, 2008, the contents of which are hereby incorporated by reference in their entirety.

FIELD OF THE INVENTION

The present invention generally relates to detection of molecules, especially detection of molecules such as chemical warfare agents, while reducing or avoiding false alarms.

BACKGROUND OF THE INVENTION

The sensing of analytes (such as chemical warfare agents, etc.) with considerable sensitivity and specificity is a requirement in many circumstances. Sensitivity is required to sense analytes before their level reaches an undesired value. Specificity is necessary to avoid false positives that would engender unnecessary, costly, and potentially dangerous responses.

Chemical warfare agents are lethal compounds applied to warfare have been developed over many years, some derived from commercial compounds used to control destructive animals, insects, and plants, others are toxic industrial chemicals, such as chlorine, that also have been used in warfare. Still others are the product of military research and development intended to produce lethal agents of desired characteristics and effects.

The complexity and variety of chemical compounds, many only slightly different in structure or chemical reactivity, make the task challenging. False positive such as may originate from similar compounds present in the sampled environment are a source of concern.

For detecting certain molecules (such as chemical warfare agents, etc.), there are various conventional sensors and detectors that have been previously provided. However, these existing sensors and detectors are not without flaws and shortcomings. For one, there is wanted greater sensitivity, namely, the ability to detect on the order of parts per trillion (ppt).

Significantly, current sensors and detectors tend to have a false alarm (false positive) problem, namely, that the sensors and detectors are triggered not just by what is wanted to be detected but also triggered by "interferents." For example, in the case of current sensors used by the chemical agent detector community, benzene and toluene are potential interferents. These chemicals are components of JP-8 and diesel fuel vapors and exhaust and associated with a variety of burning materials and gunfire. False alarm problems have been reported in the testing of currently used fieldable chemical agent detectors in the presence of JP-8 and diesel vapor and exhaust, as well as toluene. In these tests a positive detection of either nerve or blister agents was registered when neither of these chemical warfare agents was present.

Another example where sensitivity and specificity are needed is in sensing compounds in the environment that are destructive to the atmosphere and water and endanger the health of those exposed. In other cases chemical sensing is important for the collection of information about criminal and foreign military developments and operations. In industrial operations, chemical sensing is necessary to recognize when dangerous processes may be incompletely contained, becoming uncontrolled, and/or potentially creating a HAZMAT release.

There have not yet been provided, but are wanted, fieldable devices with sensors that are both sufficiently sensitive and versatile to provide for detection of a variety of important threat agents and simultaneously discriminating of, or insensitive to, interferents which would register false positives.

Also, there are needs for detecting toxic materials in water samples. The safety of drinking water is of importance for military deployments in combat zones. Domestically there is the treat of terrorist attacks against water supply systems. A large concern is the protection of populations against toxic chemicals that find their way into drinking water, and into lakes, rivers, bays and oceans where they harm animals and fish, and damage recreational uses of such natural resources.

SUMMARY OF THE INVENTION

The present inventor has provided an elegant solution to the difficult problem of how to minimize false positive readings in a sensor, preferably while detecting the analyte or target molecules (such as, e.g., chemical warfare agent, etc.) at the desired sensitivity. The invention provides for preprocessing (such as, e.g., inventive molecular separation) to be performed on a sample to sort molecules from the sample before a sensor (such as, e.g., a carbon nanotube bundle sensor) is operated on what remains of the sample.

The operation of an inventive molecular separator advantageously allows the molecular separator to function simultaneously as a concentrator by drawing the sample through the invention as a continuous flow, at each instant trapping the desired molecules. This allows the analyte or analytes thereby selected to accumulate in ever increasing numbers to a degree proportional to the amount of time the sample flow is maintained. Thus a variety of different sensors can be employed, varying in their specific characteristics, and regardless of limits on the minimum concentration of analyte needed for them to produce a measurable electrical or other signal relatable to the concentration of the intended analyte.

An objective of the present invention is to provide a physical discriminant to reduce false positives, that of molecular size. In some cases, such providing of a physical discriminant may suffice to select only the desired compound from among the many possibly present and exposed to a chemical sensor. In other cases, additional a priori reasoning may be further performed to reduce or eliminate potential interfering compounds (also known as "interferents") based on external circumstances of the site where the measurement is being made and other information available remotely. In this invention, preferably a chemical sensor is embedded in, and is a part of, a system created for some larger purpose. In a significant class of applications, site-specific information can be drawn upon to manage the sensor and interpret the sensor's results.

The present invention recognizes and makes use of the fact that the sizes of molecules of concern in many sensing applications bear a close relationship to the sizes of atomic-level nanostructures such as, e.g., those of carbon nanotubes. Regularly-spaced columnar nanostructures can serve as molecular size filters for external flows.

The invention in one aspect provides a method of sorting molecules by size, comprising: contacting at least one nanotube having an inner diameter within a first predetermined diameter range, with an initial sample (such as, e.g., an initial sample that is a gaseous sample; an initial sample of air; etc.) of various-sized molecules, to produce a screened sample; such as, e.g., inventive methods further comprising contacting at least one nanotube of an inner diameter within a second predetermined diameter range which is not equal to the first predetermined diameter range, to a screened sample to produce a size-sorted sample (such as, e.g., inventive methods wherein the at least one nanotube is contained within a first screen comprising a plurality of nanotubes having the first predetermined diameter range, and the at least one nanotube having the second diameter is contained within a second screen comprising a plurality of nanotubes having the second predetermined diameter range).

In another aspect, the invention provides a method of reducing an initial sample (such as, e.g., an initial sample that is a gaseous sample) that contains various-sized molecules to a subset of molecules of a predefined size range, comprising: screening the initial sample to produce a screened sample consisting of molecules of size smaller than a maximum size (such as, e.g., a size D(max)); and requiring molecules of size smaller than a minimum size (such as, e.g., a size D(min)) to exit, such as, e.g., inventive methods comprising producing a target sample consisting of molecules having a size in a range of D(min) to D(max); inventive methods wherein the step of screening the initial sample to produce a screened sample consisting of molecules of size smaller than the maximum size (such as, e.g., D(max)) includes applying a screen comprising at least one nanotube having an inner diameter to exclude molecules bigger than the maximum size; inventive methods wherein the step of requiring molecules of size greater than the minimum size (such as, e.g., D(min)) to exit includes applying a screen comprising at least one nanotube having an inner diameter that permits passage of molecules below the minimum size (such as, e.g., D(min)); inventive methods comprising passing the initial sample through a screen comprising at least one nanotube having an inner diameter to exclude molecules bigger than the maximum size, followed by withdrawing, through a screen comprising at least one nanotube having an inner diameter that permits passage of molecules below the minimum size (such as, e.g., D(min)), a subset of molecules which are smaller than the minimum size (such as, e.g., D(min)), such as, e.g. inventive methods comprising performing the withdrawing step until the initial sample has been transformed into a target sample consisting only of molecules of the predefined size range; inventive methods comprising screening an initial sample that is a gaseous sample; inventive methods comprising a screening step of screening an initial sample comprising at least one of an analyte molecule and/or a molecule that evokes a false positive for the analyte molecule; inventive methods comprising a screening step of screening an initial sample comprising at least one pair of an analyte molecule and/or a molecule that evokes a false positive for the analyte molecule and is of a different size than the analyte molecule; inventive methods practiced with a selective screening structure that comprises: a first screen comprising at least one nanotube having a first diameter; a second screen comprising at least one nanotube having a second diameter which is smaller than the first diameter, wherein the selective screening structure has a size selectivity in a range between a minimum which equals about the second diameter and a maximum which equals about the first diameter; and other inventive methods.

The invention in another aspect provides a method, comprising: for an initial sample (such as, e.g., an initial sample that is a gaseous sample; an initial sample that includes at least one of an analyte molecule and/or a molecule that evokes a false positive for the analyte molecule; etc.) that contains various-sized molecules, reducing the initial sample to a subset of molecules of a predefined size range (such as, e.g., a reducing step that sorts from the initial sample molecules which are outside of a size range), and bringing the subset of molecules of the predefined size range into contact with at least one sensor (such as, e.g., a carbon nanotube bundle sensor; a sensor configured to detect a chemical warfare agent; etc.), such as, e.g., inventive methods wherein the initial sample includes at least one of an analyte molecule and/or a molecule that evokes a false positive for the analyte molecule; inventive methods wherein the initial sample includes at least one of an analyte molecule and/or a molecule that evokes a false positive for the analyte molecule, and the reducing step sorts the molecule that evokes a false positive; inventive methods wherein the initial sample includes a set of molecules that are of a relatively large size, a set of molecules that are of a relatively small size, and a target set of molecules that are of a medium size which is the predefined size range, and the reducing step reduces the initial sample to the target set; inventive methods wherein the reducing step comprises a step of screening-out too-big molecules and further comprises a step of requiring too-small molecules to exit while screening-in target-size molecules; inventive methods wherein the reducing step sorts at least one molecule that would evoke a false positive and prevents the molecule that would evoke the false positive from coming in contact with the sensor; and other inventive methods.

In another aspect, the invention provides a method of sorting, from an initial sample (such as, e.g., an initial sample that is a gaseous sample), a subset of molecules that would activate false positives by a sensor which is intended to detect a molecule or molecules, comprising: for the sensor, identifying a size range of the analyte molecule or molecules; sorting, from the initial sample, molecules outside the identified size range of the analyte molecule or molecules (such as, e.g., a sorting step that comprises sorting molecules sized outside the size range of the molecules intended to be sensed, before the sensor is applied; a sorting step that comprises applying at least a first screen comprising at least one nanotube of an inner diameter that excludes too-big molecules, and further comprises requiring too-small molecules to exit through at least one nanotube of an inner diameter that permits passage of too-small molecules; and other sorting steps), such as, e.g., inventive methods wherein applying the first screen includes applying a first screen that comprises an array of nanotubes of an inner diameter that excludes too-big molecules, and wherein requiring too-small molecules to exit includes requiring too-small molecules to exit through a second screen that comprises an array of nanotubes of an inner diameter that permits passage of too-small molecules; inventive methods wherein the requiring too-small molecules to exit includes operating a pump to create a flow of sample; and other inventive methods.

For example, in an inventive method, when the class of molecules to be sensed is that of nerve gases, the two filter sizes would be such that molecules smaller than 1.320 nm are allowed to enter the concentrator/sensor cell and molecules smaller than 0.727 nm are allowed to exit from the concentrator/sensor cell (with these mentioned sizes corresponding, respectively, to the smallest and largest sizes of nerve agents, GB (sarin) at the small end of the selected range and the nerve agent VX at the large end of the size range).

The invention in another aspect provides a method of processing an initial sample (such as, e.g., an initial sample that is a gaseous sample; an initial sample of air; etc.) of a set of molecules before contact with a sensor, comprising: directing the initial sample of the set molecules into contact with an entry screen leading into a container, the entry screen excluding from entry a subset of molecules bigger than a molecular size range of molecules wanted to be detected by the sensor;

withdrawing from the container a subset of molecules smaller than the molecular size range of molecules wanted to be detected by the sensor; such as, e.g., inventive methods further comprising operating the sensor in the container after the directing and withdrawing steps; inventive methods wherein the initial sample includes at least one molecule that would evoke a false-positive and after the directing step and the withdrawing step, the molecule that would evoke a false-positive is not within the container; inventive methods wherein the initial sample includes at least one molecule that would evoke a false-positive and at least one molecule that is intended to be detected by the sensor, and after the directing step and the withdrawing step, the molecule that would evoke a false-positive is not within the container and the molecule that is intended to be detected by the sensor is within the container; and other inventive methods.

In another aspect the invention provides a molecular separator comprising: a chamber comprising at least a first screen and a second screen; the first screen comprising at least one nanotube having an inner diameter that is a first diameter or within a first range of diameters; the second screen comprising at least one nanotube having an inner diameter that is a second diameter or within a second range of diameters, which is smaller than the first diameter or first range of diameters; such as, e.g., inventive molecular separators further comprising: an inlet valve upstream of the chamber, a pump downstream of the chamber and an exit portal through which molecules being separated-out as too small exit the chamber; inventive molecular separators further comprising a sensor (such as, e.g., a carbon nanotube bundle sensor) disposed within or inserted into the chamber.

The invention in a further aspect provides a molecular separator which separates molecules of a class defined by a specified physical characteristic, such as, e.g., inventive molecular separators that separate molecules that are in a gaseous medium; inventive molecular separators that separate molecules while distinguishing between molecules of other classes having similar physical characteristics; inventive molecular separators that distinguish between molecules having a specified parameter greater than a D(min) and less than a D(max); inventive molecular separators that include a sensor to produce a quantitative measure of the concentration of the defined class of molecules in the range of 1 ppm (part per million) to 1 ppt (part per trillion); inventive molecular separators that can be used in both urban and rural locations; inventive molecular separators that separate molecules in a time period of less than 5 minutes; man-portable inventive molecular separators; inventive molecular separators that can be used in an automated or semi-automated mode of operation; and other inventive molecular separators.

In another aspect the invention provides a method of nanotube screening, comprising: vaporizing to convert analytes that may be present in the sample as liquid phase droplets to reduce such droplets to a vapor phase, and nanotube screening after vaporizing.

The invention in another aspect provides a method of assessing whether a sensor which has returned a positive indication is false-alarming, comprising: when the sensor has returned the positive indication for presence of a target substance, operating a software-based query sequence in which a series of yes/no queries are presented to a human user for yes/no response, wherein each yes/no query tends to screen for whether the target substance is actually present and being detected by the sensor or whether instead the sensor could issue a false alarm.

In a further aspect the invention provides an interactive interrogator system for detecting a target substance, comprising: a sensor tuned to detect the target substance; and a computer-based interrogator system that is interactive with a user and that provides a series of interactive queries that when answered by the user tend to screen for whether the sensor is indeed detecting the target substance or could be detecting a non-target substance that would cause a false alarm.

In another aspect, the invention provides a sensor-based method of detecting an analyte (such as, e.g., tabun, soman, cyclosarin, etc.), such as, e.g., inventive detecting methods that comprise a step of subjecting an initial sample to a length separation operation (such as, e.g., a subjecting to a length separation step that sorts the initial sample into a size-sorted sample including a mid-sized sample) in advance of a step of operating the sensor (such as a sensor for an analyte) to take a measurement (such as, e.g., a step of operating the sensor to take a measurement of the mid-sized sample), followed by an ambiguity-resolving step (such as, e.g., an ambiguity-resolving step performed with respect to the mid-sized sample for which the measurement was taken in the step of operating the sensor); and other inventive sensor-based detecting methods that reduce false alarms to a low level.

In another aspect, the invention provides for detecting toxic materials in water samples.

BRIEF SUMMARY OF THE DRAWINGS

FIG. 1 is a cross-sectional schematic showing a detector concept according to an embodiment of the invention in which the inventive screens (≡) are particularly noted.

FIG. 1A shows a cross-sectional schematic view of a nanotube which is a preferred component of a screen in FIG. 1, with a molecule small enough to pass through the nanotube also shown. As a general state of affairs, analytes will be elongated rather than spherical, as shown here schematically. However as a result of their rapid kinetic motion and their frequent collisions with one another and with the containing walls, they have both translational and rotational kinetic energy. Thus an analyte, though it has an elongated shape, is treated as a minimum-size circumscribing sphere for addressing the relative size of an analyte and a nanotube through which it travels.

FIG. 2 is a part of a table which may be used in practicing the invention in an embodiment where a target molecule is tabun, soman and/or cyclosarin; other than the rows for tabun, soman and cyclosarin which are nerve agents, the two leftmost columns in FIG. 2 indicate interferents. In FIG. 2, the data for the nerve agents and interferents include a standard chemical identification number, molecular weight, melting point, boiling point, vapor pressure, chemical formula, and the maximum diameter. In FIG. 2, the rows have been sorted by maximum diameter and are shown in increasing order of the diameter of a minimum circumscribing sphere.

In FIG. 3A, numbering from FIG. 1 is repeated where applicable.

FIG. 5 is a flow chart for an inventive embodiment which includes an ambiguity-resolving step 502.

DETAILED DESCRIPTION OF A PREFERRED EMBODIMENT

Figure 3:
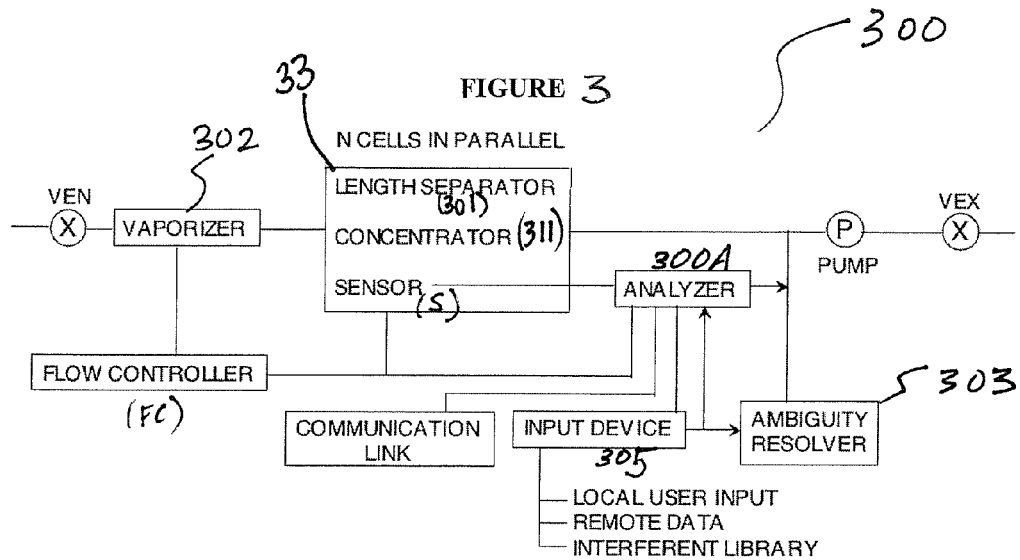
FIG. 3 is a block diagram that shows components used in constructing a system 300 which is an inventive embodiment including at least one cell 33.

The invention may be appreciated with reference to the figures, without the invention being limited thereto. Referring to FIGS. 1-1A, a detector concept may be appreciated, according to which may be constructed a system 100 useful for detecting an analyte molecule (such as, e.g., an analyte molecule which is a chemical warfare agent; etc.). "Analyte" is used herein according to its ordinary meaning in the chemical arts and refers to a substance or chemical constituent which is the subject of an analysis. An analyte substance might also in the literature be called a target substance.

The system 100 includes a sensor 1 which can detect the analyte molecule, such as, e.g., a carbon nanotube (CNT) sensor. As some examples for use as sensor 1, sensors useable as sensor 1 are known and commercially available, such as, e.g., a sensor having electrical properties that change with exposure to an analyte. However, before this invention, the state of the art for fieldable devices had not yet provided sensors both sufficiently sensitive and versatile to detect a variety of important threat agents and simultaneously discriminate or be insensitive to interferents which could register an excessive number of false alarms, which problem system 100 addresses, improving the specificity of a conventional sensor when used as sensor 1 within system 100 compared to stand-alone use of the same sensor.

In system 100, the sensor 1 is disposed within a chamber 2. According to the invention, in system 100, the chamber 2 housing the sensor 1 is divided into an upstream section 21, a section 22 near the sensor 1, and a downstream section 23. Particularly, the system 100 is constructed to be sensitive to an analyte molecule size, such as, e.g., considering the length of the analyte molecule. For example, if the analyte molecule is a nerve gas, nerve gases are in the length range of 0.727 to 1.320 nm, the chamber 2 is divided to take into account that the analyte molecule is in a length range of 0.727 to 1.320 nm. The system 100 is tuned (such as, e.g., maximum length dimension-wise) to analyte molecule size by providing a screen 10 that excludes all molecules bigger than the size (such as, e.g., length) of the analyte molecule, and by providing a screen 11 that permits to pass all molecules smaller than the size of the analyte molecule. For example, if system 100 is being constructed for an analyte molecule that is a nerve gas, the screen 10 is a screen that excludes all molecules with length greater than 1.320 nm and the screen 11 is a screen that permits passage of all molecules with length less than 0.727 nm.

Referring to FIG. 1, an initial sample is introduced via inlet 3 into the system 100, and molecules smaller than the analyte molecule make their way to downstream section 23, while molecules bigger than the analyte molecule remain in upstream region 21. Only molecules in the size range of the analyte molecule accumulate in region 22 near the sensor 1. In the case of an analyte molecule which is a nerve gas which is a range of about 0.727 to 1.320 nm, a system 100 is constructed for use in a method in which the system 100 performs a reducing step that sorts from an initial sample introduced via inlet 3 into the system 100 molecules which are outside of a range of about 0.727 to 1.320 nm, requires molecules which are bigger than 1.320 nm to remain in the upstream region 21, and only permits molecules which are in the range of 0.0727 to 1.320 nm to accumulate in the region 22 near the sensor 1.

In system 100, for screens 10, 11, screens comprising carbon nanotubes are preferred with screen 10 and screen 11 each being constructed with respective dimensions. FIG. 1A shows a cross-sectional view of a nanotube being used in screen 10. Each carbon nanotube used in the screen 10 has a wall thickness, such as wall thickness 10$t$ is 0.26 nm which is the diameter of a carbon atom. The outer radius 10R of the carbon nanotube in screen 10 is shown. For practicing the invention, the inner diameter of a nanotube is used. The inner diameter of a nanotube is the outer diameter (such as twice the outer radius 10R) minus the wall thickness (such as 10$t$), with some small adjustment made to reduce the effect of van der Waal's forces or interactions that might impede the motion of the sampled molecules through the nanotube filter. An example of such a small adjustment is, e.g., to increase the effective size of the analyte to be sensed, and which is used in the selection of the inner diameter of the carbon nanotube filters, by an amount sufficient to reduce the likelihood of wall interactions impeding the movement of the analyte molecules in the sample.

When a nanotube is being used within a screen that excludes molecules of a maximum size, the nanotube should have an inner diameter to exclude molecules bigger than the maximum size. When a nanotube is being used within a screen that permits passage of molecules of a minimum size, the nanotube should have an inner diameter that permits passage of molecules below the minimum size. It will be appreciated that the inner diameter of a nanotube being used within a screen 10 or a screen 11 is not necessarily set exactly equal to the molecule size which is to be excluded or permitted passage, respectively. The precise requirements are established by increasing the effective size of the analyte to be sensed, and which is used in the selection of the inner diameter of the carbon nanotube filters, by an amount sufficient to reduce the likelihood of wall interactions impeding the movement of the analyte molecules in the sample.

Much experimental evidence exists that molecules can easily pass axially through nanotube structures when the molecule is smaller than the internal diameter of the nanotube.

For example, one can be certain that a molecule that is 1.05 nm in diameter will not find its way easily through a carbon nanotube that is exactly 1.05 nm in inner diameter; therefore, if passage of molecules that are 1.05 nm in diameter is wanted, then an inner diameter of the nanotube through which the 1.05 nm diameter molecules are to pass should be slightly larger than 1.05 nm diameter being an example when constructing a screen to be used to permit passage of molecules by an amount indicated above.

Screens 10, 11 (FIG. 1) preferably comprise more than one nanotube. It will be appreciated that within one screen, all nanotubes are not required to be of absolutely identical inner diameter; a range of inner diameters is permissible for nanotubes within one screen as long as they do not admit or pass molecules that would engender excessive false alarms.

A screen 10, 11 optionally may comprise a compound filter that comprises two or more carbon nanotube arrays in series, such as two carbon nanotube arrays in series comprising a first carbon nanotube array which differs from a second nanotube array as to respective size screening. A compound filter may be used to sharpen size sorting capability of a screen 10 or a screen 11.

An example for constructing system 100 is to use macro size technology for the sensor 1, MEMS technology for the chamber 2, and nanotechnology for the screens or filters 10, 11.

The inventive system 100 of FIG. 1 advantageously may be used for sensing analyte molecules using the sensor 1 while excluding interferent molecules from being sensed by the sensor 1, of a size suited to the sizes of nanotube filters that can be constructed.

The present invention provides an elegant solution addressing the problem of false positives returned by a sensor configured for an analyte (such as, e.g., sensor 1 in FIG. 1), such as, e.g., inventive positioning of screens or filters (such as, e.g., filters constructed of carbon nanotubes) relative to the sensor 1 to limit the sensor 1 to being exposed to molecules within a defined range of sizes, with molecules bigger than the defined range being excluded from reaching the sensor by one filter 10, and with molecules smaller than the defined range being caused to exit (such as, e.g., pumped) through another, finer filter 11 before the sensor 1 is operated.

The system 100 (FIG. 1) may be used, e.g., for sorting different-sized molecules into three size categories including relatively-big molecules, molecules of target-size (such as, e.g., molecules of a size of nerve gases), and relatively-small molecules.

Referring to system 100, in which too-big molecules accumulate in upstream section 21 and analyte molecules accumulate near the sensor 1, after the sensor 1 has been applied to make a measurement, if the system 100 is to be re-used on a new initial sample, first the system 100 should be evacuated such as by back-flushing.

In using an inventive system 100 (FIG. 1), the likelihood that the sensor 1 is sensing an interferent rather than the analyte molecule will be greatly reduced compared to using a stand-alone sensor such as the sensor being used as sensor 1. However, in some cases, there will still exist the possibility, albeit reduced, of a false positive, i.e., that the sensor 1 in system 100 is responding to presence of an interferent rather than presence of an analyte molecule. Approaches for resolving whether an interferent is present include, e.g., an assessment of the environment in which the system 100 is operating (such as, e.g., a visual determination by a human user that the sources of the interferent are not present); an ambiguity resolver which is a second sensor dependent on a different physical parameter. The computer-based ambiguity resolver is preferred.

For example, in the course of operating an inventive sensor-based system (such as, e.g., system 100, system 300 (FIGS. 3-4), etc.), a response of a sensor (such as, e.g., sensor 1 (FIG. 1), sensor S (FIGS. 3-4), etc.) is obtained through a step 500 (FIG. 5). In many cases necessarily there is ambiguity whether the sensor response has been activated by an analyte or, rather, by an interferent. Therefore, preferably the step 500 of obtaining the sensor response is followed by an ambiguity-resolving step 502 (such as, e.g., an ambiguity-resolving step which comprises a visual assessment of the environment in which the sensor is operating; an ambiguity-resolving step which comprises operating a computer-based system; an ambiguity-resolving step including observations by a human user and prompting by a computer-based system; an ambiguity-resolving step which includes querying by a computer-based system having stored therein a library (such as, e.g., a library of computer-readable data relating to analytes and interferents) wherein the computer-based system wherein the computer-based system queries at least one human user and receives input from the human user; etc.

When the inventive system 100 (FIG. 1) is used to sort molecules in an initial sample into too-big molecules, molecules of target size, and too-small molecules, optionally, sorted molecules of target-size may be subjected to further processing such as at least one further chamber (not shown in FIG. 1) that is specifically configured (such as through at least one additional sensor which is different from sensor 1) to measure whether an interferent is present or interferents are present.

The invention may also be used, e.g., in environmental applications, first responder applications, hazardous materials applications, chemical intelligence, law enforcement, etc.

The invention also may be applied to detecting and measuring the concentration of toxic chemicals in water, such as, e.g., by inventive systems and methods according to FIG. 7 (which is further discussed in Inventive Example 5 below). Such an application to water samples requires, in addition to adequate sensitivity, chemical sensors that operate in water. The principles of the invention as described for working with air samples are adapted with minor modification to the case of water samples. The separator and concentration steps work as well with water as air. In addition to seeing large toxic molecules, the length separators see, instead of a large number of molecules of nitrogen, oxygen, carbon dioxide, and other atmospheric components, an equivalently large number of water molecules. In the case of applying the invention in water, the water flow is arranged so that after the selector/concentrator cells have collected enhanced levels of analytes of interest, the water is flushed out and replaced with air. Thus instead of an integrated separator/concentrator cell having the chemical sensor inside (as shown in FIG. 1), the sensor is in a separate cell that always remains dry. Thus the modification consists of establishing "plumbing" for two separate fluid flow paths. One is wet and sees water and analytes. The second is dry and sees air and the concentrated analytes. Additional valves are used. In this application, the issue now is not false positives triggering unnecessary defensive responses but rather the identification of the potentially wide range of toxic chemicals present. Time is no longer an issue because the water flows are continuous and no immediate responsive action is required. Generally the detector in this application does not have the severe limits on size, weight, power, and speed that tactical warning or intelligence collection missions impose. A second sensor, such as a mass spectrometer or other sensor, may be used for ambiguity resolution.

The invention may be appreciated with reference to the following examples, without the invention being limited thereto.

INVENTIVE EXAMPLE 1

Detector Concept

By "sensor" herein we mean a device placed in a concentration cell, such as a sensor which is a nanotube sensor. We do not use the words "sensor" and "detector" interchangeably.

Referring to the accompanying FIGS. 1-1A, in system 100 a valve V11 at the entry point is opened so that an entryway which is upstream region 21 may receive the initial sample (which in this example is a gaseous sample, such as a sample of air of unknown composition). What ultimately is wanted is for the sensor 1 (such as a carbon nanotube (CNT) bundle sensor) to perform its actual sensing as would be done conventionally, but without being burdened by encountering molecules which give false positives and are not themselves wanted to be detected. However, at the same time, it is wanted, e.g., for the sensor 1 to be able to detect if an analyte molecule is present, even if present on the order of only parts per billion or trillion.

In this inventive example, the analyte molecules are considered and a size range is established for the analyte molecules. The inventive preprocessing is to sort too-big molecules and too-small molecules from the initial sample and only present molecules in a size range for the analyte molecules to the sensor 1. Referring to the figure, the initial sample encounters a first screen 10 (the left-most screen), said first screen 10 blocking entrance into a chamber 22 in which the sensor 1 is disposed for operation in due time. Preferably, the first screen 10 comprises a plurality of nanotubes each of a diameter to prohibit passage of too-big molecules. For example, in the case where nerve gases are the analyte molecules for the sensor, the first screen excludes molecules with length greater than 1.32 nm.

Preferably a further preprocessing is performed, by applying a second screen 11 as shown in FIG. 1 (the right-most screen), which is a screen through which too-small molecules may pass but through which molecules within the size range established for analyte molecules cannot pass. For example, in the case of nerve gases, the screen 11 for permitting exit of too-small molecules would permit molecules with length less than 0.927 nm to exit the chamber 22 in which the sensor 1 is disposed. For example, methane which is about 0.3 nm would exit. Preferably there is provided a valve V12 and a pump P downstream of the screen 11 that permits too-small molecules to exit, and the valve V12 is opened and the pump P is operated to urge or require too-small molecules to exit the chamber 22 in which is disposed the sensor 1.

For practicing the invention, it is preferable that the range of sizes of analyte molecules to be sensed by a single sensor 1 be in a relatively narrow range, that is, that the analyte molecules to be sensed by sensor 1 are relatively close in size. For example, tabun, soman and cyclosarin which are nerve agents are relatively close in size, and a single inventive system 100 comprising sensor 1 sensing tabun, soman and cyclosarin as analyte molecules may be constructed.

INVENTIVE EXAMPLE 1A

Likewise to the manner that a molecular separator structure was provided in Inventive Example 1 configured for screening-out non-nerve gas molecules for use with a nerve gas sensor, it readily can be appreciated that other respective molecular separator structures likewise can be made with each molecular separator structure configured for its own agent.

Preferably, the respective molecular separator structures each tuned to a respective analyte molecule are placed in parallel.

INVENTIVE EXAMPLE 1B

Packaging Various Collections of Functionalities to Accommodate Different Domains of Applicability and User Requirements 1. Multiple size ranges or continuous spectrum of size measurement
   a. Each Range $L_1$-$L_2$ is defined by two CNT filters represented by a radius $R_1$ and $R_2$. Multiple ranges measured simultaneously can be accommodated by feeding each range of a common manifold.
   b. Each pair of CNT filters in a parallel analysis manifold can be either:
      i. Factory-installed
      ii. Field depot-installed
      iii. User-installed
2. Form factor can be understood in terms of current "smart" cell phones.
   a. Touch sensitive screen for both function set selection, status readout, and output display.
   b. Built in comm capability to enable receipt of local status of forces information, weather models, adjacent detector warnings with map location, and other advisory or backup data
   c. Scrolling by page shifting touch
   d. Magnification by two-finger motion or selection by one-finger touch.
   e. Backlit screen
   f. Icons to reduce literacy requirement and provide language transportability in combined military operations
   g. Provision for downloading data to a central processor that can be
      i. Separately worn or carried by user
      ii. Carried by other personnel
      iii. Manned or Unmanned Ground, Sea or Air vehicle mounted
      iv. At a base prior to leaving on mission
   h. Battery recharging cable. Power sources can be in the above locations (i-iv)
   i. Incorporation of camera to send ancillary data to central location for analysis to minimize need to record information on surroundings.
   j. GPS function handles all geolocation tasks
   k. Target size and weight range of 3-16 oz.
   l. Direct downloading of software to field unit for function updating or to add field applications as wanted via a military version of an "iTunes" store
   m. Wireless, packet switching, anti-jam, and/or burst communications
3. Additional Features/capabilities can be incorporated:
   a. Field changes of battery
   b. Clips and other attachment devices for user or vehicular use
   c. Solar cell for battery recharging
   d. Field or depot changeout of CNT filter pairs
   e. Insertion of CNT sensors
   f. Voice input/output Examples of user modes include, e.g.,
   a. Military missions where risk of attack must be considered. This implies need for user stealth, small size, operation by user in protective clothing
   b. Field intelligence collection where size and weight requirements can be relaxed, with suitable/flexible packaging
   c. Environmental area survey
   d. Incorporation of detector into a user local area net
   e. Commercial chemical plant HAZMAT safety
4. Architectures
   a. Detector architecture such as the U.S. Department of Defense Common CBRN Sensor Interface (CCSI's specifications to allows for families of compatible and interoperable devices) are important
   b. A communications architecture to fit the detector into an existing or specified communications network
   c. An information architecture to define data formats and with interfaces to support two-way transmission of e.g., data, software, warning, etc.
   d. A logistics architecture to include
      i. Device identification
      ii. Device location
      iii. Device user or organization association
      iv. Calibration of detector
      v. Status and maintenance condition vi. Field diagnosis of malfunction vii. Field repair such as resetting, recalibration, switching to built-in redundant backup capability viii. Logging past locations, past readings, malfunctions, change in operator or organizational assignment ix. Incorporation of ancillary sensing functions such as temperature, humidity, impact, sound level, light level x. Flexible growth of detector with time to incorporate new or improved physical devices, software-defined new functionalities, replacement of damaged components 5. Seamlessly incorporate the detector into systems planned or extant of the Army, Air Force, Navy, intelligence community and other user communities including but not limited to the Environmental Protection Agency and other environmental monitoring organizations; industry associations such as water supply, industrial occupation and industrial safety; Dept intent of Homeland Security, particularly at state, county, and local levels; Federal Emergency Management Agency (FEMA); Commercial Chemical plant safety; education and training groups for university level (teaching and laboratory safety) and training (industrial, military, law enforcement, first responders, disaster response, etc.); transportation security needs such as passenger, baggage or freight inspector; incorporate nuclear radiation sensor for border control to protect against nuclear weapons and radiological threats; etc.

INVENTIVE EXAMPLE 1C

Another inventive example is as follows. Call the section between the first two valves, that contain two size filters $L_1$ and $L_2$ with a sensor in between a "cell" $C_{12}$. If P is the pump that draws the gas being measured, then the detector can be denoted as —$C_{12}$—P—.

There are other physical configurations possible that lead to enhanced functionality. Suppose one wants to produce a continuous "spectrum" of molecular lengths: 1-2, 2-3, 3-4, ... N–(N+1) between molecular length 1 and length N+1. These would logically be in series, and denoted as:

—$C_{12}C_{23}C_{34} \ldots C_{N(N+1)}$—P—

Another useful geometry would meet the military need to classify a detected agent in a way that would assist in adopting appropriate protective measures. For this there are three categories of agents of common concern:

Blood agents: CK (cyanogen chloride; chemical formula CNCl) and AC (hydrogen cyanide; chemical formula HCN). These are quite small, of the order of 0.4-0.5 nm. To detect them one must select that length range.

Another set of agents are the blister agents such as L (lewisite; chemical formula $C_2H_2AsCl_3$) are intermediate in length. Lewisite is 0.9 nm while sulfur mustard ($C_4H_8Cl_2S$) is about 1 nm long. There are various formulations of sulfur mustard, differing in being mixed with other materials to enhance its effects under various conditions.

In this case, therefore, one could make a sensor that distinguishes between the three classes, blood, blister, and nerve agents by selecting three ranges: 0.4-0.5, 0.9-1.0, and 1.1-2.2 nm. In this case they would be connected in parallel and each fed off a common manifold, and each using the same suction pump.

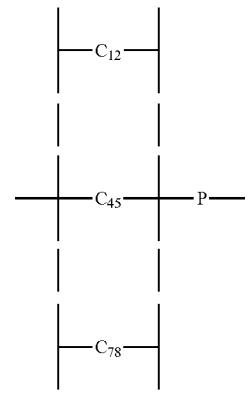

There can be combinations of serial and parallel cell arrangements chosen and fabricated to fit particular user needs. For example, since the size range of nerve agents is so large, one may want to divide it more finely, breaking down the 1.1-2.2 nm range into a continuous length spectrum of four or five sub-pieces.

Another variation is to use either a second suction pump or the same suction pump with a more complex set of valves and "piping" to feed any of the contents of any of the concentration chambers between the CNT length filters into a separate section C* based on other molecular parameters and using a sensor or sensors responsive to other physical properties such as dipole moment, chemical reactivity reactivity, etc. (C* may be configured in series and parallel, not shown.) This could be drawn as:

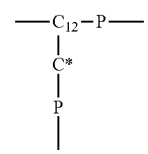

(For simplicity, without showing all valves).

The electronics may include other functions and be structured with an open architecture to allow the device to become a subsystem of a larger system or to provide a basis for adding on other subsystems to it.

INVENTIVE EXAMPLE 2

Operation of Flow Controller

A system 300 (FIG. 3) that receives air is constructed, comprising a pump (P) to draw in air containing the analyte or analytes. The system 300 further comprises at least one length separator 301 that selects molecules in a selected size range. The system 300 further comprises a concentrator 311 integrated with each separator 301, wherein concentrator 311 and length separator 301 may be the same component. The system 300 further comprises a sensor (S) integrated with each separator 301, the sensor (S) being a suitable sensor to detect the target analyte or analytes. The system 300 also comprises an analyzer 300A to interpret the sensor outputs from each separator 301. The system 300 further comprises an interactive interrogator 305 which is a computer-implemented system or device (such as, e.g., an interactive interrogator that receives at least one of user inputs from a human user or users and/or receives data from a remote system and/or receives or contains a library in a computer-readable form of analytes and possible interferents). Also the system 300 comprises a flow controller (FC) to manage operation of the separator, concentrator 311, ambiguity resolver 303 if any, and to manage backwash operations including operation of the valves VEN, V11, V12, VN1, VN2, V3, V4, V5, VEX and the pump (P). The system 300 further comprises a vaporizer 302 to convert liquid-phase analytes in an airflow to vapor phase. Optionally the system 300 comprises an ambiguity resolver 303.

Figure 4:
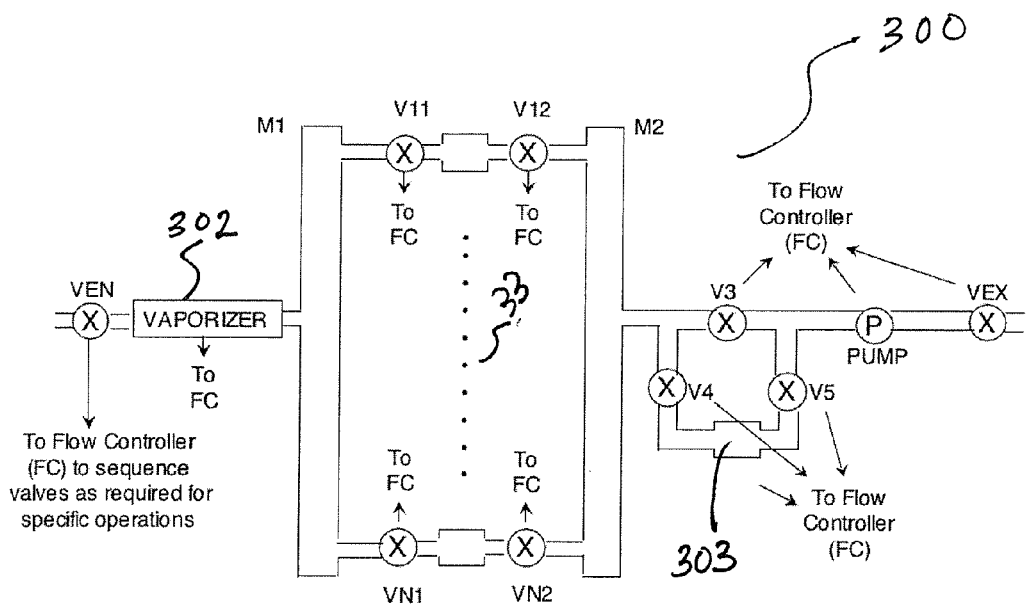
FIG. 4 is a diagram of an inventive system 300 corresponding to FIG. 3.
Figure 3A:
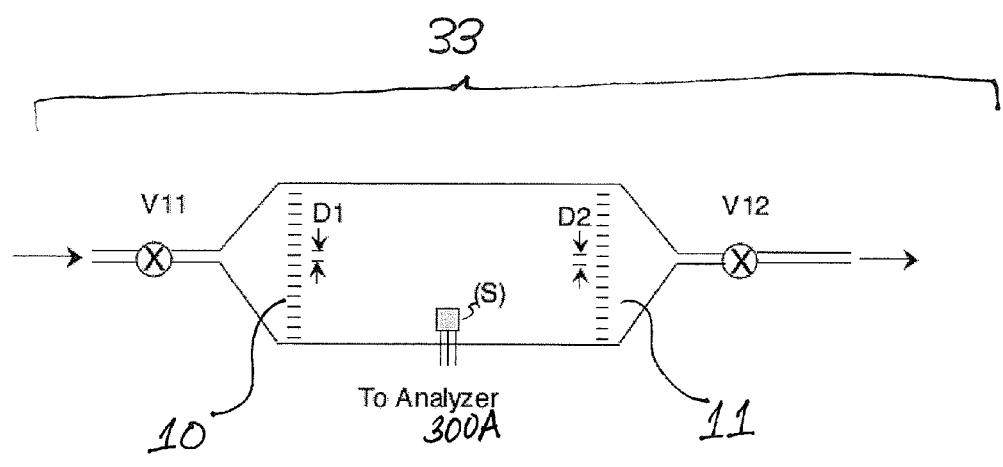
FIG. 3A is a cross-sectional schematic of a cell 33 useable in system 300 (FIG. 3).
Figure 6:
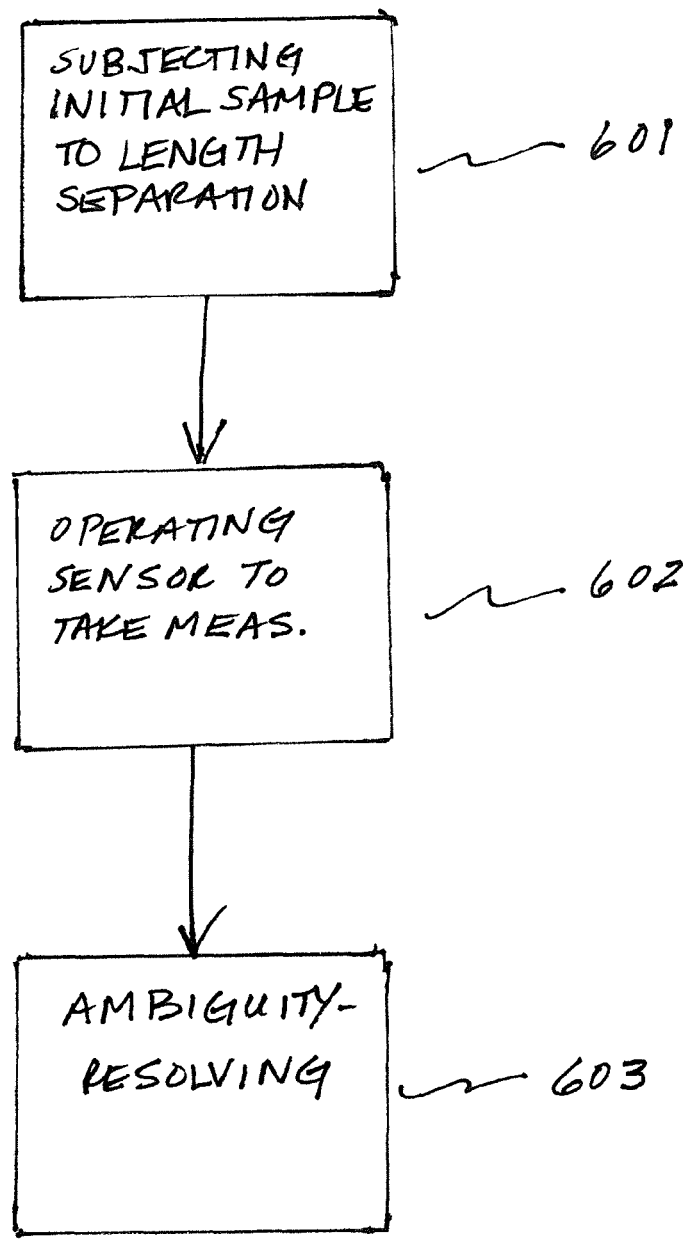
FIG. 6 is a flow chart for an inventive reduced false-alarm, sensor-based method of detecting an analyte which comprises a step 601 of subjecting an initial sample to length separation; a step 602 of operating a sensor to take a measurement; and an ambiguity-resolving step 603.

In FIGS. 3-4, N cells 33 are in parallel of which an example of a cell 33 is shown in FIG. 3A.

Referring to FIG. 3, a pump (P) draws in a fluid to be sampled. The pump (P) has a volumetric capacity of R vol/sec. The system 300 comprises an entrance valve VEN and an exit valve VEX. Valves VEN and VEX are connected to the flow controller (FC). By varying the size, weight, and power consumption of the pump (P) used in system 300, the size, weight, power sensitivity, and measurement time of the system 300 can be varied.

Referring to FIGS. 3-4, one or more separators 33 are connected in parallel to an entrance manifold M1. In FIG. 4, the number of separators 33 illustrated is merely representational of "N", where N is an integer 1 or greater. A separator 33 may also be referred to as a separator cell 33.

A separator 33 has an entrance face which consists of an array of roughly parallel nanotubes open at both ends and oriented in the direction of the flow of the sampled fluid, each of roughly the same inner diameter and roughly the same length, thus constituting a molecule filter. The inner diameter D1 of each entrance face (i.e., the first) nanotube filter is equal to the minimum diameter of molecules to be excluded from said separator 33. D1 is chosen to be slightly larger than that of the diameter of the analyte molecule or molecules. "Diameter of the molecule" means the maximum diameter swept out by a molecule rotating about an arbitrary axis through the center of mass of the molecule subject to normal thermal collisions before encountering the first nanotube filter.

The exit face of the separator 33 consists of an array of roughly parallel nanotubes open at both ends and oriented in the direction of the flow of the sampled fluid, each of roughly the same inner diameter and roughly the same length thus constituting a second molecule filter. The inner diameter D2 of the exit face nanotubes are such that D2 equals the maximum diameter of the molecules not to be retained in said separator 33 but instead allowed to exit said separator 33.

The separator cell 33 (FIGS. 3-4) thus selects molecules whose maximum diameter D falls within the range D1>D>D2. On one of the walls of the cell 33 is a sensor (S) that produces an electrical signal that is a function of the concentration of the analyte molecule or molecules in the sampled fluid drawn through by the pump (P). Such electrical connections as required are passed through a wall of a chamber enclosing the sensor (S), to the outside, and are available for connection to the analyzer 300A.

A valve V11 at the entrance of the first separator cell of the separator cells 33 and a valve V12 at the exit of the first separator cell of the separator cells 33 is then closed by a flow controller (FC) when the analyzer 300A determines that the analyte's or analytes' concentration measurement is complete, or after a maximum pumping time set by the user. When there is more than one separator cell 33, this step is performed for each of the cells 33 at a time determined by the analyzer 300A, or after a maximum pumping time set by the user.

In order for the fluid sample containing the analyte or analytes to be removed from the cell 33 when commanded by the user at the conclusion of the measurement in preparation for a subsequent fluid sample to be introduced into the cell, valves V11, V12 and VEN are opened, VEX is closed, and the cell 33 is cleansed of the analyte or analytes through backflushing. Table 1 shows the position of each of the valves in the system 300 in the shut down state, during the measurement time, during operation of the ambiguity resolver 303, and during the backwash operation.

TABLE 1

| Valves and Pump | Shut-down state | Measurement operation | Ambiguity Resolution state (illustration for Cell 1 only) | Back-flush operation |
|---|---|---|---|---|
| VEN | closed | open | closed | open |
| V11 | closed | open | closed | open |
| V12 | closed | open | open | open |
| VN1 | closed | open | closed | open |
| VN2 | closed | open | closed | open |
| V3 | closed | open | close | open |
| V4 | closed | closed | open | open |
| V5 | closed | closed | open | open |
| VEX | closed | open | closed | closed |
| Pump | off | on (inflow) | on (inflow) | on (outflow) |

For the system 300 in FIGS. 3-4, using at least one cell 33 (FIG. 3A), Table 1 shows whether each of valves VEN, V11, V12, VN1, VN2, V3, V4, V5, VEX is closed or open and whether the pump (P) is off or on for different respective states and operations including a shut-down state, a measurement operation, an ambiguity resolution state and a backflush operation. In Table 1, the column for Ambiguity Resolution state is an illustration only for one cell 33.

Each separator cell 33 acts as a concentrator to increase the sensitivity of the system 300. For a separator cell 33 having a volume V, the pump (P) will fill this volume V in a time T=V/R where R is capacity of the pump (P). For a configuration having N cells 33 in parallel, each cell 33 the same size, the time to fill all of the cells 33 is T=NV/R. Further suppose that the desired sensitivity of the measurement of each cell 33 is a concentration of molecules of c/unit volume but the maximum sensitivity of the sensor (S) is only s molecules/unit volume. It will be necessary to fill the cell 33 volume repeatedly to achieve a concentration ratio CR that is s/c times greater, each time retaining the analyte or analytes until the cell 33 volume has sufficiently concentrated the analyte or analytes such that the sensor (S) is able to register their presence. Therefore $$TR = V \times N \times s/c$$

in which operational requirements of the system 300 will set T, c, and N. Therefore the pump capacity R is set by the cell volume V and the maximum sensitivity, s, of the sensor (S).

The sensor (S) in an integrated sensor/concentrator cell 33 operates in the following manner. A sensor (S) has a resistance that is altered by the attachment of an analyte molecule to a surface of the sensor (S) or to an internal structure of the sensor (S) forming one wall of the separator/concentrator cell 33. At least two electrical connections including the two ends of a resistive element extend through a wall of the cell 33 and connect to the analyzer 300A.

The analyzer 300A consists of an electronic data processor. The analyzer 300A comprises a voltage source that applies a voltage to each sensor (S). Each respective sensor (S) in each of the cells 33 need not be identical in material or construction to another sensor (S). The analyzer 300A also has a voltage measuring capability that records the change in resistance of the sensor (S) with exposure to the analyte or analytes in the cell 33. The analyzer 300A comprises a clock that provides a time base against which to measure resistance changes and based on which measurements and actions performed by the system 300 are time-tagged. The analyzer 300A comprises an algorithm that recognizes resistance changes in the sensor (S) as a function of time, interprets this change in terms of chemical concentration, and determines a response of sensor (S) in accordance with procedures specified by the user through the interactive interrogator 305. The analyzer 300A comprises a display, such as a display that provides three colored green/yellow/red lights viewable by a user for each of the respective cells 33 in which green indicates that no analyte or analytes above a user-specified alerting threshold are present, yellow indicates that some analyte or analytes are present above a user-specified threshold, and red indicates that a user-specified dangerous level of analyte or analytes is present. The analyzer 300A comprises a logic element that generates required signals for the flow controller (FC) to open and close valves. The analyzer 300A comprises logic elements based on which the system 300 provides more detailed information to the user through a display that is part of the interactive interrogator 305 and is commanded by the user. The analyzer 300A comprises a logic element that communicates such information as the user may have indicated to be supplied to a communications device for transmission to a higher level sensor/response system of which system 300 is a subsystem or component.

The system 300 further comprises an interactive interrogator 305 which receives commands of a user. Interactive interrogator 305 provides environmental information to the user and analyzer 300A to determine a response, or range of responses, to be provided to the user through the display. The interactive interrogator 305 may comprise, e.g., a receiver for GPS coordinates; a communication capability for establishing connection with a wind sensor; a digital camera; etc. Examples of environmental information that the interactive interrogator 305 provides (such as providing in computer-readable form) to the analyzer 300A are, e.g., GPS coordinates of the sensor (S) at the time a measurement is made; wind speed and direction (provided either by user measurement or estimate or from a wind sensor or database); environmental information relating to presence of possible chemical interferent sources needed by the analyzer 300A to make correct deductions from measurements taken by sensor (S) and downloaded to the analyzer 300A (which environmental information relating to presence of possible chemical interferent sources may be downloaded to the analyzer 300A from a remote database); a library of chemical compounds consisting of precursors or products (such as, e.g., a library of chemical compounds consisting of precursors or products derived from actual activities observed by the user to be present); etc. In addition, a digital camera may optionally be used to produce images, such as, e.g., images reviewable by a remote user at a different location away from the sensor (S) to evaluate the interferent potential presented by the environment in the vicinity of the sensor (S).

In the system 300, the flow controller (FC) opens and closes valves, controls the flows into and out of the single or multiple cells 33, controls the operation of vaporizer 302, controls the flow to an optional ambiguity resolver 303, and controls back-flush of the system 300 following a measurement by sensor (S). The flow controller (FC) receives status information from the analyzer 300A when a cell 33 has completed a measurement, when the at least one cell 33 is to be emptied in preparation for a next measurement sample, and when the user requests information from the ambiguity resolver 303.

Under the temperature and pressure conditions when the measurement or measurements are made by the sensor (S), analytes can be in either a vapor phase or can be small droplets of liquid phase. To be certain that such analytes that are liquid droplets as may be present are completely measured, on entry into the system 300 they pass through a vaporizer 302 that emits electrical, laser, thermal energy or other means sufficient to vaporize liquid phase analytes if any.

INVENTIVE EXAMPLE 2A

Ambiguity resolution

Referring to Example 2 and system 300, it is possible that upon completion of an analyte's or analytes' concentration measurement in a cell 33, there maybe ambiguity as to whether the separated vapor is an analyte or interferent. In such a case of a potential false positive, optionally the analyzer 300A communicates this status onwards, such as, e.g., communicating this status to the user for handling or the status is directly presented by the flow controller (FC) to an ambiguity resolver 303. In the case in which the status is directly presented by the flow controller (FC) to ambiguity resolver 303, the exit valve VN2 on the cell or cells 33 that are registering are sequentially opened. Valve V3 is closed and valves V4 and V5 are opened and the concentrated samples contained therein are presented to a follow-up sensor (not shown in FIGS. 3-4) which is not sensor (S), which follow-up sensor is capable of making a further determination based on a different physical property of the molecule or molecules than was sensed by sensor (S), with information relating to the different physical property being contained in the library.

This example a system 300 which includes a length separator 301 further includes an ambiguity resolver 303 which is a hardware-based ambiguity resolver consisting of a sensor responsive to a physical characteristic (which is not a length characteristic) of an analyte or analytes.

INVENTIVE EXAMPLE 3

Reducing False Positives in Sensing Chemical Warfare Agents (CWA)

A preliminary spreadsheet was prepared for over 1700 compounds including chemical warfare agents and the rest chemicals derived from an analysis of the list of DoD "interferents," e.g. burning rubber and the chemical compounds derived from those processes. The DoD interferents are illustrative of combat operations and various chemicals such as arising from vehicles and housekeeping materials typically found in closed spaces. Information such as chemical names, structural formula, molecular weight, melting point, boiling point (to know what are gases at standard temperature and pressure), and vapor pressure was compiled.

Using molecular modeling software, maximum diameters of circumscribing spheres were calculated and tabulated.

From the preliminary spreadsheet, the false positive situation, namely, potential vapor phase false positives could be seen using molecular length as the primary selection criterion. Based simply on molecular length, there were 51 possible interferents.

INVENTIVE EXAMPLE 3A

Ambiguity Resolution by Means of a Second Physical Sensor

Although other alternative approaches for reducing the number of false positives in Example 3 may be possible, the preferred approach is to use a second selection criterion to rule out the possibility of a false positive. This has the advantage of not having to rely on local circumstances, local judgments, and local expertise.

An example of a second selection criterion is molecular weight, such as by using in series with the CNT length selector, a mass spectrometer.

Table 2 is based on a length-first selection dividing the length range in the preliminary spreadsheet from 0.63 nm to 1.39 nm into two ranges, 0.63 to 0.97 nm and 1.04 nm to 1.39 nm. One then brackets the molecular weight of the chemical agents in each of these length ranges from smallest to largest and looks to see if any of the interferents still fall into the joint selection range. The results for this example are:

TABLE 2

| LENGTH RANGE (NM) | LENGTHS SELECTED (NM) | TOTAL LENGTH RANGE (NM) | MOLECULAR WEIGHT RANGE | NO. OF CHEMICAL AGENTS IN RANGE | NO. OF INTERFERENTS IN RANGE (LENGTH ONLY) | NO. OF INTERFERENTS (LENGTH PLUS MW) |
|---|---|---|---|---|---|---|
| 1 | 0.63-0.97 | 0.34 | 140-180 | 5 | 32 | 2 |
| 2 | 1.04-1.39 | 0.35 | 198-239 | 5 | 19 | 0 |

Examples 3-3A illustrate how to select detector parameters based on the problem being addressed.

Upon applying the joint selection criteria of Examples 3-3A, only two residual interferents got through the joint selection criteria, 1,2 dichlorobenzene and isopharone. Therefore through Examples 3-3A, the number of interferents has been substantially reduced from the beginning number.

INVENTIVE EXAMPLE 4B

Application of Library of Analytes and Interferents

For constructing a table with rows that include at least one analyte and include interferents for that analyte, the following columns may be used: interferent source, chemical derived therefrom (from these two columns, a local user can indicate what is not present); molecular weight; melting point, boiling point (these columns are used to tell solid from vapor from liquid); vapor pressure (possibly to rule out a compound); maximum diameter, of which the columns for interferent source and maximum diameter are considered most important.

In FIG. 2, the rows have been sorted by maximum diameter and are shown in increasing order of maximum diameter. Of the columns in FIG. 2, interferent source and maximum diameter are considered most useful for designing systems, methods, devices and apparatuses according to the invention.

INVENTIVE EXAMPLE 5

Detecting Analytes in Water Samples

Figure 7:
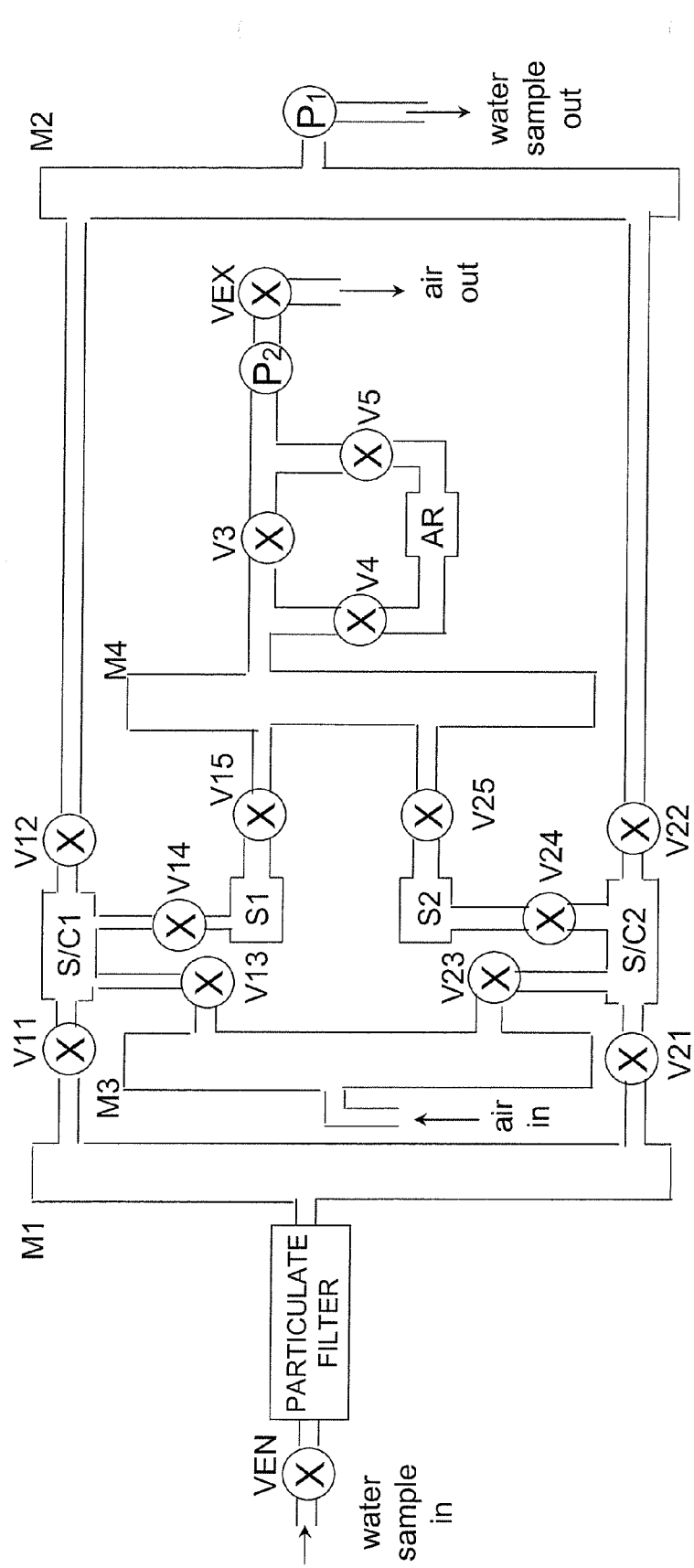
FIG. 7 is a diagram for an inventive embodiment in which water samples are processed.

Referring to FIG. 7, the water being sampled is drawn continuously under suction produced by pump P1 through the selector/concentrator cells S/C. For this to occur, valve VEN, V11 and V12 are open, as well as the corresponding valves on the other selector/concentrator cells selected for use. In FIG. 7 only two S/C are shown for simplicity, S/C1 and S/C2 so that V21 and V22 are open also.

The water flow (FIG. 7) continues as with the air sampling case. Each selector/concentrator cell has two molecular-length defining pairs of CNT filters, one at the entrance and one at the exit of the cell as shown in FIG. 1. In this way molecules of a specified size range are captured and retained.

The sampled water first enters manifold M1 (FIG. 7) from which it flows to the active selector/concentrator cells and the outflow from each of the selector/concentrator cells is collected in manifold M2 prior to exiting the apparatus through valve VEX which is open. The only feature different from the air case is that bodies of water will have a variety of types and sizes of particulate matter. These must be excluded lest they clog the CNT filters and so a conventional particulate filter is shown after entrance valve VEN and before manifold M1 (FIG. 7). The pore size of this conventional filter is chosen based on the size of the particulates present in the sampled water. Typically it will be of the order of 1 micron.

Valves V13 and V14 (FIG. 7) are closed, as well as the corresponding valves for S/C2 which is similarly constructed but with CNT filters selected to be of a size that a different desired molecular length range is defined. In FIG. 7 as shown in FIG. 4 there is no limit to the number of selector/concentrator cells that may be operated in parallel beyond the ultimate practical limits on size, cost, and power.

As with air sampling, pump P1 (FIG. 7) is operated for a time set by the user, that time being selected to increase the sensitivity of the apparatus such that it will be able to register toxic materials at levels deemed harmful.

When the pumping time has been reached, pump P1 is closed down as well as valves V11 and V21 (in this example of two selector/concentrator cells in use.) The apparatus is now filled with water in what might be called the "water loop." The water in the selector/concentrator cells contain, in addition, concentrated analytes whose molecular size falls within the CNT filter-defined length ranges. All other parts of the apparatus are dry. At this point the analytes have not been presented to a sensor and thus have registered no signal, for the reason that no suitable sensors capable of operating in an aqueous environment are available.

The next step is to drain out the water from the selector/concentrator cells. This is done by restarting the pump P1 and opening valves V13 and V23. This allows the water to be pulled out of the water loop of the apparatus and replaced by air that flows into each active selector/concentrator cell through manifold M3. When this is completed, V12 and V13, are closed and valve V14 is opened, valve V15 remaining closed, and the corresponding valves on S/C2 operated similarly. This results in the air enriched with analytes extracted from the water sample in S/C1 being exposed to sensor 51, and similarly for S2. Because the partial pressure of the analytes in S/C1 is greater than that in S1, which is devoid of analytes, mixing will occur and S1 (FIG. 7) will be able to respond with the same kind of electrical signal as in the case of the air sampled flow in FIG. 4. The speed of this mixing could be increased by heating S/C1 to increase the pressure of the gases therein should this be deemed important for a particular sampling application. This part of the apparatus can be called the "air loop."

When the measurement of the analyte concentrations in the selector/concentrator cells is completed, the apparatus must be cleared to prepare it for the next water sample. This sample could be in a different field location, or the same location at some later time, or for a next sample to be measured in a central measurement laboratory undertaking this kind of analysis as an internal service or as a commercial service.

At this point there are two ways of proceeding. If the measurement is deemed to be unambiguous, valves V13, V15, V3, and VEX are opened, with V4 and V5 remaining closed, and pump P2 pulls the air into manifold M4 and out of the apparatus and the subsequent flow cleans all the analyte in S/C1 and S1 from the air loop. This process is repeated sequentially for all the other selector/concentrator cells employed.

If, however, there is an ambiguity in the measurement from S1, V3 is closed and valves V4 and V5 opened and pump P2 presents the ambiguity sensor with the analyte or analytes from S1. This process is repeated for all the other selector/concentrator cells employed requiring ambiguity resolution.

In addition to back-flushing the air loop, the water loop must be back-flushed. This is done by opening VEN, V11, V12, and the corresponding valves on S/C2 and all other active selector/concentrator cells. Pump P1 is then reversed and it pushes sample water through the water loop. The CNT filters do not impede the cleaning of each selector/concentrator cell since the analyte molecules can flow back through the CNT filters past which they entered.

At this point all valves are returned to their initial position and the apparatus is ready for the next sample.

The following Table 2 summarizes the valve positions and pump operation for the several states of the apparatus. The information is, for simplicity, shown for the case of only one active selector concentrator dell, S/C1:

TABLE 2

| VALVES AND PUMPS | SHUT-DOWN STATE | WATER SAMPLING | DRAIN SEL/CONC CELL | MOVE ANALYTES TO AIR LOOP SENSOR | AMBIGUITY RESOLUTION | BACK-FLUSH AIR LOOP | BACK-FLUSH WATER LOOP |
|---|---|---|---|---|---|---|---|
| VEN | closed | open | closed | closed | closed | closed | open |
| V11 | closed | open | closed | closed | closed | closed | open |
| V12 | closed | open | open | closed | closed | closed | open |
| V13 | closed | closed | open | open | closed | open | closed |
| V14 | closed | closed | closed | open | closed | closed | closed |
| V15 | closed | closed | closed | closed | open | open | closed |
| V3 | closed | closed | closed | open | closed | open | closed |
| V4 | closed | closed | closed | closed | open | open | closed |
| V5 | closed | closed | closed | closed | open | open | closed |
| VEX | closed | closed | closed | closed | closed | open | closed |
| P1 | off | on(suction) | on(suction) | on(suction) | off | off | on(pressure) |
| P2 | off | off | off | off | on(suction) | on(suction) | off |

While the invention has been described in terms of a preferred embodiment, those skilled in the art will recognize that the invention can be practiced with modification within the spirit and scope of the appended claims.

What I claim is:

1. An interactive interrogator system for detecting a target substance, comprising:
   a concentration cell;
   a first sensor tuned to detect the target substance in a range of 1 ppm to 1 ppt, but that may provide a false alarm for an interferent, wherein the first sensor comprises at least one nanotube and the first sensor is situated in the concentration cell;
   a second sensor which is an ambiguity resolver and which is dependent on a different physical parameter than the first sensor, wherein the second sensor is in a separate cell outside where the first sensor is located;
   a computerized interrogator that is interactive with a human user, wherein when the first sensor has returned a positive indication for presence of a target substance, the interrogator performs steps comprising:
      presenting a query sequence to the human user for response,
      as the user makes response, receiving response data,
      processing the response data including screening for whether the target substance is actually present in the concentration cell and being detected by the first sensor or whether instead the first sensor is likely to be issuing a false alarm;
   wherein the interrogator is connected to the ambiguity resolver;
   a library in a computer-readable form of at least the target substance and possible interferents, wherein the library is contained in or receivable by the interrogator.

2. A system into which is received an initial sample of various-sized molecules which are to be sorted by size, wherein the initial sample comprises at least one of an analyte molecule to which a first sensor is tuned and/or a molecule that upon coming in contact with the first sensor evokes a false positive for the analyte molecule; the system comprising:
   an inlet through which the initial sample is received into the system;
   a container;
   a first valve that when opened permits the initial sample to be received into an upstream section of the container;
   a first screen which is an entry screen that is encountered by the initial sample and that comprises an array of nanotubes of an inner diameter that excludes molecules based on size from entering the container,
   a second screen, downstream of the first screen and comprising an array of nanotubes of an inner diameter that permits molecules smaller than the second screen to exit the container and blocks molecules bigger than the second screen;
   the first sensor, disposed in the container to only be in contact with a subset of molecules of a predefined size range bounded by a size range defined by the first screen and the second screen;
   a pump downstream of the second screen;
   a second valve that when opened, and when the pump is operated, permit too-small molecules to exit the container;

a second sensor which is an ambiguity resolver and which is dependent on a different physical parameter than the first sensor, wherein the second sensor is in a separate cell outside where the first sensor is located.

3. The system of claim 2, wherein the container is divided into an upstream section, a section near the first sensor, and a downstream section.

4. The system of claim 2, including a library in a computer-readable form of at least
 a target substance which is the analyte to which the first sensor is tuned; and
 a set of possible interferents.

5. The system of claim 4, wherein the library comprises entries for:
 AFFF;
 Ben Gay;
 cigarette smoke;
 diesel exhaust;
 diesel vapor;
 explosion site;
 fresh cut grass;
 glue;
 high risk TIC;
 low risk TIC;
 mineral brake fluid;
 nerve agent;
 paint;
 wood smoke.

6. The system of claim 4, wherein the library comprises entries for:
 α-Cubebene;
 α-Terpinene;
 allyl isothiocynate;
 anisaldehyde;
 cyclosarin;
 diethylene glycol;
 diethyl methylphosphonate;
 ethyl benzene;
 ethyl chlorothioformate;
 ethyl cyclohexane;
 hexachlorocyclopentadiene;
 hexane;
 isobutyl chloroformate;
 Limonene;
 3-methyl heptane;
 methyl salicylate;
 n-butyl chloroformate;
 n-butyl isocyanate;
 nicotine;
 Nonafluorobutanesulfonoyl fluoride;
 p-Cymene;
 propyl benzene;
 propylene glycol t-butyl ether;
 soman;
 styrene;
 tabun;
 tetraethyl lead;
 Terpinen-4-ol;
 thiodigylcol;
 v-Terpinene.

7. The system of claim 2 further comprising a flow controller.

\* \* \* \* \*